US005876434A

United States Patent
Flomenblit et al.

[11] Patent Number: 5,876,434
[45] Date of Patent: Mar. 2, 1999

[54] IMPLANTABLE MEDICAL DEVICES OF SHAPE MEMORY ALLOY

[75] Inventors: Josef Flomenblit; Nathaly Budigina, both of Holon, Israel

[73] Assignee: Litana Ltd., Holon, Israel

[21] Appl. No.: 910,030

[22] Filed: Aug. 12, 1997

[30] Foreign Application Priority Data

Jul. 13, 1997 [IL] Israel ......................................... 121316

[51] Int. Cl.⁶ .............................. A61F 2/06; A61C 13/12
[52] U.S. Cl. .................................... 623/1; 623/12; 433/172
[58] Field of Search ................................... 623/1, 12, 16; 433/172, 173, 225

[56] References Cited

U.S. PATENT DOCUMENTS

| | | |
|---|---|---|
| 3,786,806 | 1/1974 | Johnson et al. |
| 4,485,816 | 12/1984 | Krumme . |
| 4,665,906 | 5/1987 | Jervis . |
| 5,037,427 | 8/1991 | Harada et al. . |
| 5,067,957 | 11/1991 | Jervis ........................................... 623/2 |
| 5,147,370 | 9/1992 | McNamara ................... 623/1 |
| 5,190,546 | 3/1993 | Jervis ....................................... 623/1 |
| 5,421,955 | 6/1995 | Lau ........................................ 606/198 |
| 5,562,641 | 10/1996 | Flomenblit et al. . |
| 5,624,508 | 4/1997 | Flomenblit et al. . |

OTHER PUBLICATIONS

Cragg et al., Title: Percutaneous Arterial Grafting; Radiology, vol. 150, No. 1. pp. 45–49, Jan. 1984.

*Primary Examiner*—Michael J. Milano
*Attorney, Agent, or Firm*—Gary M. Nath; Nath & Associates

[57] ABSTRACT

A medical device which comprises a shape memory alloy (SMA) portion which is deformable from an undeformed first configuration assumed by it in an austenitic state of the SMA to a deformed second configuration, whereby the SMA is converted into a strain-induced martensite or partial martensite. This conversion increases the temperature of transformation ($A_s$) from an initial transformation temperature $A_s°$ to a temperature $A_s'$. When the SMA, once in the second configuration, is heated to a temperature higher than $A_s'$, it transforms to an at least partial austenite and it transforms towards the undeformed first configuration with a decrease of $A_s$ from $A_s'$ to $A_s°$. $A_s°$ is below body temperature such that when the device is deployed in the body, after placing it in its target location with the SMA portion in the second configuration and then heating it to assume its first configuration, the SMA is stable in the at least partial austenite at body temperature.

14 Claims, 2 Drawing Sheets

IMPLANTABLE MEDICAL DEVICES OF SHAPE MEMORY ALLOY

FIELD OF THE INVENTION

This invention relates to implantable medical devices, and more particularly, to implantable shape memory nitinol devices which are thermally expanded from a strain-induced martensitic state to a stable austenitic state.

BACKGROUND OF THE INVENTION

Implantable medical devices, such as stents, heart valves, bone plates, intrauterine contraceptive devices and the like must meet many requirements to be useful and safe for their intended purpose. For example, they must be chemically and biologically inert to living tissue and to be able to stay in position over extended periods of time. Furthermore, devices of the kind mentioned above must have the ability to expand from a contracted state, which facilitates insertion into body conduits or cavity, to a useful expanded diameter. This expansion is either accomplished by a forced expansion, such as in the case of certain kinds of stent by the action of a balloon-ended catheter, or by self-expansion such as by shape-memory effects.

A widely used metal alloy for such applications is the nickel-titanium alloy, known as "nitinol". Under certain conditions, nitinols can be highly elastic such that they are able to undergo extensive deformation and yet return to their original shape. Furthermore, nitinols possess shape memory properties such that they can "remember" a specific shape imposed during a particular heat treatment and can return to that imposed shape under certain conditions.

The shape memory effect of nitinols results from metallurgical phase transformations. Certain nitinols are characterized by a transition temperature or transition temperature range, above which the predominant metallurgical phase is termed "austenite" and below which the predominant metallurgical phase is termed "martensite". The transformation temperature from austenite (or austenitic state) to martensite (or martensitic state) is termed "martensitic transformation"; the reverse transformation from austenite to martensite is termed as "austenitic transformation". The transformations occur over a range of temperatures and are commonly discussed with reference to $M_s$ and $M_f$, the start and finish temperatures of the martensitic transformation, respectively, and $A_s$ and $A_f$, the start and finish temperatures of the austenitic transformation, respectively. Transformation between these two phases is reversible such that the alloys may be treated to assume different shapes or configurations in the two phases and can reversibly switch between one shape to another when transformed from one phase to the other. In the case of nitinol medical devices, it is preferable that they remain in the austenitic state while deployed in the body as nitinol austenite is stronger and less deformable and thus more resistant to external forces as compared to nitinol martensite.

Implantable medical devices made of nitinol have been known in the art. See for example U.S. Pat. Nos. 3,786,806, 4,485,816 and 5,037,427. In U.S. Pat. No. 5,562,641, a two-way shape memory effect is employed such that the austenitic transformation temperature is above body temperature and the martensitic transformation temperature is below body temperature, whereby the device retains its last conditioned state (e.g. austenite or martensite) at body temperature. U.S. Pat. No. 5,624,508 discloses a method for the manufacture of shape memory alloy (SMA) device with defined transformation temperature. In many such devices, $A_s$ is considerably above body temperature and accordingly for converting the device into the austenitic state, it is necessary to provide heat in an extent which in addition to being difficult to apply may be damaging to the surrounding tissue. In devices where $A_s$ is only slightly above body temperature, the austenite may become destabilized, e.g. as a result of a stress-induced martensitic transformation, rendering the device less resistant to external stresses.

In many conventional nitinol medical devices, there is often a large temperature range between $A_s$ and $A_f$, which thus makes it difficult to establish, in an accurate and reproducible manner, the extent of the austenitic transformation upon heating.

The use of stress-induced martensite principle, rather than temperature-induced martensite, has likewise been employed in medical devices, e.g. in U.S. Pat. No. 4,665,906. In such devices, austenitic nitinol is deformed to form stress-induced martensite and held in its deformed configuration and martensitic state by a restraining member. The device is introduced into the body in the deformed configuration, where it is removed from the restraining member to return to its austenitic state and configuration without any temperature change. In the case of such a device a restraining member has to be employed and once the medical device is released from the restraining member, it is almost instantly deployed. If the device is not accurately positioned immediately before release from the restraining member, it may have to be removed with some damage to the surrounding tissue.

SUMMARY OF THE INVENTION

The present invention relates to implantable medical devices such as stents, heart valves, bone plates, clips, tooth implants, catheters, intrauterine contraceptive devices and the like.

In the following, the term "shape memory device" will be used to denote a device which is made entirely or having at least a functional portion made of a shape memory alloy (SMA). The term "functional portion" denotes a portion of the device which is of prime importance to the functioning of the medical device. A shape memory device utilizes the shape memory properties of SMA for its function: the entire device or at least the functional portion changes in its configuration as a result of switching its metallurgical phase from austenite to martensite and, if desired, also vice versa. The term "configuration" should be understood as meaning either one or more of the shape, diameter, elasticity, tensile properties, or any other property of the SMA which affects its function within the body. The configuration is in fact a sum of such properties.

The invention provides a medical device with at least a functional portion comprising an SMA of the two-way shape memory type, namely having two different "memorized" configurations, one assumed by it in the austenitic state and the other assumed by it in the martensitic state. In addition, the device of the invention has a transition temperature from martensite to austenite ($A_s$ and $A_f$) which is strain-dependent, namely it increases after deformation (a strain-induced change in configuration). The deformation thus yields a strain-induced martensite which gives rise to an increase of $A_s$ (which is below body temperature in an undeformed state) to $A_s'$. Once converted in the body to austenite $A_s$ resumes to its original temperature value ($A_s^\circ$) whereby the device is stabilized in the austenitic state.

The invention provides, by a first of its aspects, a medical device comprising a shape memory alloy (SMA) portion having an austenitic and a martensitic state with a different configuration in each of these states, the SMA being transformable from a martensitic to an austenitic state by an austenitic transformation occurring in a temperature range between $A_s$, a start temperature of the austenitic transformation, to $A_f$, a finish temperature of the austenitic transformation, and being transformable from an austenitic state to a martensitic state by a martensitic transformation occurring in a temperature range lower than body temperature between $M_s$, a start temperature of a martensitic transformation and $M_f$, a finish temperature of the martensitic transformation, $A_s$ being lower than body temperature in an undeformed state; the device being characterized in that:

the SMA portion is deformable from an undeformed first configuration assumed by it in the austenitic state to a deformed second configuration, such that the deformation converts it into a strain-induced martensitic or partial martensite with an increase in $A_s$ from its original temperature $A_s°$, to a temperature $A_s'$; and in that when the SMA portions, once in said second configuration, is heated to a temperature higher than $A_s'$, it transforms to an at least partial austenitic state, which transformation results in a change in configuration from the deformed second configuration towards the undeformed first configuration and in a decrease of $A_s$ from $A_s'$ to $A_s°$, such that the SMA portion is stable in the at least partial austenitic state at the body temperature.

The invention provides by a second of its aspects a method of deploying a medical device within the human body, the medical device comprising a shape memory alloy (SMA) portion having an austenitic and a martensitic state with a different configuration in each of these states and having associated $M_s$, $M_f$, $A_s$ and $A_f$ temperatures, being start and finish temperatures of the SMA's martensitic transformation and the start and finish temperature of the SMA's austenitic transformation, respectively, $A_s$ having the value $A_s°$, which is less than body temperature, when the medical device is in an undeformed state, and $M_s$ being less than $A_s$, the method comprising the steps of:

deforming the medical device by straining it from an undeformed first configuration assumed by it in the austenitic state to a deformed second configuration, said deforming resulting in an increase in $A_s$ from $A_s°$ to $A_s'$, the SMA portion being in a strain-induced martensitic state after said deforming;

positioning the medical device to a target location within the body, the SMA portion remaining in said strain-induced martensitic or partial martensitic state during said positioning; and transforming the SMA portion from said martensitic or partial martensitic state to at least a partial austenitic state by heating it to a temperature higher than $A_s'$, said transforming resulting in a change in the configuration of the SMA portion from the deformed second configuration towards the undeformed first configuration, the change in configuration resulting in a decrease in $A_s$ from $A_s'$ to $A_s°$ such that the medical device is stable in at least a partially austenitic state while deployed in the body.

As will be appreciated by the artisan, the increase in $A_s$ from $A_s°$ to $A_s'$ is accompanied by an increase in $A_f$ from $A_f°$ to $A_f'$.

After positioning of the medical device to a target location within the body, the SMA portion, as already noted above, is heated to a temperature above $A_s'$ following which the SMA portion transforms from the strain-induced martensitic or partial martensitic state, to at least a partial austenitic state. If the heating is to a temperature between $A_s'$ and $A_f'$, the SMA portion will undergo only a partial austenitic transformation and will thus be retained thereafter in a partial austenitic state. If the SMA is heated to a temperature above $A_f'$, it will undergo a complete austenitic transformation and will then be retained thereafter in a full austenitic state.

In accordance with an embodiment of the invention $A_s'$ is above body temperature. Typically, in such an SMA, after deformation it is converted, and retained during deployment of the device, in a totally martensitic state. Such a device can be deployed without the need for restraining members, such as required in U.S. Pat. No. 4,665,906.

In accordance with another embodiment of the invention $A_s'$ is below body temperature but $A_f'$ is above body temperature. After the straining deformation the SMA portion may be in whole or partial martensitic state.

In accordance with an embodiment of the invention, the medical device may have an original shape such that the SMA, when deformed, different portions thereof are deformed at different strains. Consequently, the $A_s'$ for different portions will thus be different. By way of illustration, a first SMA portion may have an $A_s'$ of a level $t_1$ and a second an $A_s'$ of a level $t_2$, larger than $t_1$. Thus, if the device is heated to a temperature larger than $t_1$ but less than $t_2$, the first portion will transform to an austenitic or partial austenitic state, whereas the second portion will still remain in the martensitic state. Examples of such devices are a stent with alternating portions which are in the austenitic and the martensitic states, respectively; a stent with two integral portions which are in the austenitic state with an intermediate connecting portion in the martensitic state; etc. Such a stent when deployed will have both firm portions supporting walls of an artery and intermediate flexible portions, and will thus be suitable for deployment in a curved arterial region. Another example is a stent formed with a hook-like portion, as detailed in Example 3 below. If the SMA or at least a portion thereof, which is still in the martensitic state is then heated to a temperature above $t_2$ (which is its $A_s'$ temperature) the entire SMA is then transformed into the austenitic state. In the case of a stent with a hook-like member as in Example 3, this allows easy removal or redeployment of the stent.

As will be appreciated, the two-way shape memory properties of the SMA allows, by cooling the SMA to a temperature below $M_s$, to transform the SMA to a martensitic or partial martensitic state which also allows easy removal or redeployment of the medical device.

The invention will now be further illustrated in the following detailed description of the invention and the examples with occasional reference to the annexed drawings.

DETAILED DESCRIPTION OF THE INVENTION

The device of the present invention can be made of any suitable shape memory material, preferably nitinol. The SMA in the medical device of the present invention is in at least a partially austenitic state when deployed in the body. To make a medical device in accordance with the present invention, the SMA is formed into its desired configuration and annealed at high temperatures. Regarding the manner of preparation of the SMA see U.S. Pat. No. 5,624,508 the content of which is incorporated herein by reference. The SMA is then cooled to a temperature less than $A_s$ but greater than $M_s$, such that an austenitic state is maintained. The $A_s$ of the SMA in this undeformed state, $A_s°$, is less than normal body temperature (37° C.). The medical device is then deformed to such an extent that some or all of the austenite transforms to strain-induced martensite. The SMA will remain in its deformed, martensitic or partially martensitic state typically without the use of any restraining member or the like.

Figure 1:
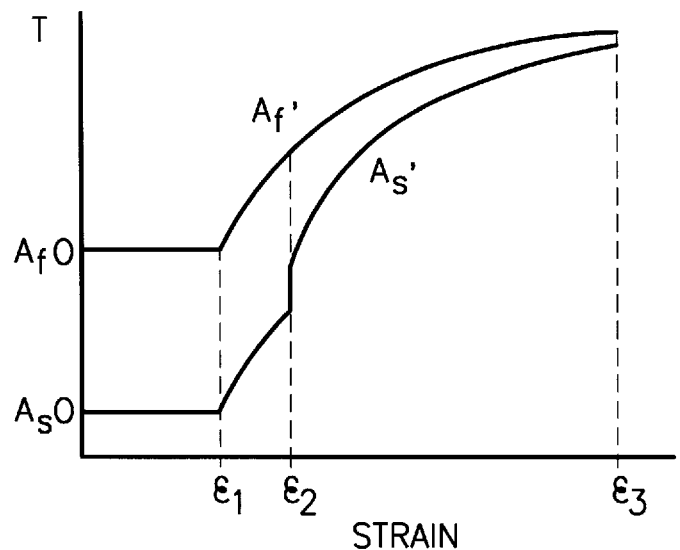
FIG. 1 shows the relationship between austenite transformation temperatures and strain for the medical devices of the present invention.

As can be seen in FIG. 1, deformation of the SMA results in an increase in the $A_s$ and $A_f$ temperatures from $A_s°$ and $A_f°$ to some $A_s'$ and $A_f'$, the extent of the increase depending on the extent of the strain. Also, as can be seen in FIG. 1, as the amount of strain increases, the difference between $A_s'$ and $A_f'$ decreases. The SMA device may typically be deformed until the $A_s$ temperature is greater than normal body temperature (37° C.) and the $A_s$-to-$A_f$ range is minimized. The device can now be inserted into the body without the need for a restraining member, and without spontaneously transforming to austenite.

The SMA may also at times be deformed such that $A_s$ increases to a temperature $A_s'$ which is less than body temperature but with $A_f'$ being above body temperature ($A_f°$ may be below or above body temperature). In such a case the SMA will only be in a partial martensitic state and its insertion may or may not require the use of a restraining member (depending on the degree of martensite).

The device is positioned at a target location, and is thereafter heated by conventional means (such as by exposure to heated saline solution flushed through a deployment catheter, by heating by means of a microwave radiation, etc.) to a temperature greater than $A_s'$, and preferably greater than $A_f'$. Accordingly, some or all of the martensite in the device will transform to austenite, thereby resulting in a change in device configuration from the deformed configuration towards the undeformed austenitic configuration. The change in configuration results in a decrease in strain, which in turn results in a decrease in $A_s$ from $A_s'$ to $A_s°$, a temperature less than body temperature. The medical device is therefore stable in at least a partially austenitic state while deployed in the body.

It is possible in accordance with the present invention to have different regions of the same medical device subjected to different amounts of deformation. These different regions will therefore have different transformation temperature such that the less-strained regions transform to austenite at temperatures lower than the regions of greater deformation. By subjecting such a medical device to an "activation" temperature greater than the $A_s'$ temperature ($t_1$) of the less-strained regions but less than the $A_s''$ temperature ($t_2$) of the higher-strained regions, it thus becomes possible to produce medical devices having regions of austenite and martensite in desired locations. The martensitic regions will be characterized by good flexibility and elasticity, whereas the austenitic regions will be characterized by high relative strength and resistance to deformation.

The present invention is further described in, but not limited to, the following examples.

EXAMPLE 1

Coil Stent

With reference to FIG. 1, an intravascular nitinol stent having features in accordance with the invention was prepared and was found to have the following transformation temperatures as a function of strain:

| Amount of Deformation | $A_s$ (°C.) | $A_f$ (°C.) |
|---|---|---|
| 0–$\epsilon_1$ | $A_s = A_s° = 28$ | $A_f = A_f° = 33$ |
| $\epsilon_2$ | $A_s = A_s' = 37$ | $A_f = A_f' = 41$ |
| $\epsilon_3$ | $A_s = A_s' = 43$ | $A_f = A_f' = 43.5$ |

The stent was heated to 35° C. and formed into a desired final configuration. The thus-formed stent was subjected to an annealing treatment and thereafter cooled to a temperature less than $A_f°$ (28° C.) but greater than the $M_s$ temperature for the alloy, thereby maintaining an austenitic state. The stent was then deformed by compressive stresses to a strain equal to $\epsilon_3$ in FIG. 1. The deformation resulted in the formation of strain-induced martensite, and a shift in $A_s$ and $A_f$ temperatures to 43° C. and 43.5° C., respectively. The compressed stent configuration facilitated easy introduction into and movement within a blood vessel in which it was deployed. A stent according to this Example was tested in pigs.

Once positioned to a target location in the body via catheter, the stent was heated to 44° C. by flushing warm saline through the deploying catheter. The heating resulted in a complete transformation to austenite and a corresponding change in stent configuration towards the desired final configuration. The change in configuration resulted in a decrease in strain to within the range 0–$\epsilon_1$ such that $A_s$ and $A_f$ were well below body temperature. The stent was thus stable in a fully austenitic state while deployed in the body.

EXAMPLE 2

Spiral Ribbon Stent

A ribbon (thickness 0.15 mm, width 2.0 mm) was rolled from nitinol (50.7 at % Ni) wire by rolling at 400° C. Then, the ribbon was mounted on a mandrel (5.0 mm diameter) to form a spiral shape with gaps between loops. To form a desired final configuration of a spiral stent with an outer diameter of 5.3 mm, the ribbon was treated at 500° C. for 1.5 hours, then at 700° C. for 0.5 hours, then at 550° C. for 0.5 hours and finally at 480° C. for 1.5 hours. After this annealing, the $A_s$ and $A_f$ temperatures of the stent were determined to be 28° C. and 33° C., respectively. The stent was then cooled to room temperature (about 25° C.) and deformed onto mandrels of varying diameter down to 1.0 mm. This deformation resulted in the formation of strain-induced martensite. The $A_s$ and $A_f$ temperatures of the stent after deforming onto each mandrel is shown in the table below:

| Stent Diameter (mm) | $\epsilon$ (%) | $A_s$ (°C.) | $A_f$ (°C.) |
|---|---|---|---|
| 4.0 | 0.8 | 28 | 33 |
| 3.0 | 2.0 | 28 | 33 |
| 2.5 | 3.0 | 33 | 38 |
| 2.0 | 4.5 | 38 | 40 |
| 1.5 | 7.0 | 42 | 43 |
| 1.0 | 12 | 44 | 44.5 |

In view of the transformation temperatures listed in the above table, the stent could be inserted into the body via catheter without a covering sheath when deformed to a diameter of 2.0 mm or less because the $A_s$ temperature was greater than body temperature (37° C.) and the stent would therefore not transform to austenite during insertion.

The stent prepared in accordance with this Example was tested in pigs as well as in human trials and deployed in the body of tested subjects in trachea, oesophagus, urethra and bile duct.

The stent was deformed to 1.5 mm diameter and positioned to a target location in a blood vessel. The stent was thereafter heated to 43° C., which resulted in a transformation to austenite and a change in stent configuration towards the desired final configuration. The final diameter of the stent when deployed in the body was approximately 4 mm such that the entire austenitic temperature transformation range was below body temperature. The stent was therefore stable in its austenitic state while deployed in the body.

EXAMPLE 3

Spiral Ribbon Stent With Removal Hook

Figure 2:
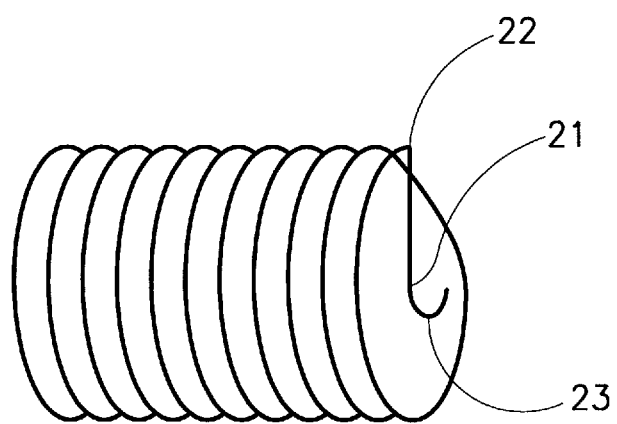
FIG. 2 shows an intravascular stent with a book-like manner as an embodiment of the present invention.

The stent as described in Example 2 was formed in its austenitic state with a hook-like member extending from the stent circumference towards the stent center (FIG. 2). When subsequently wound onto various mandrels to achieve a stent diameter of 1.7 mm, the stent was largely characterized by a strain of 5% except for the hook and stent "elbow" regions which was highly deformed while in the austenitic state in order to provide the hook-like member. The strain at the locations where the elbow regions were formed while in the austenitic state approaches 7%. The $A_s'$ and $A_f'$ temperatures of the entire stent except the hook and the elbow regions was 41° C. and 43° C., respectively.

A stent according to this Example was tested both in human trials and in pigs and deposited in the organs mentioned in Example 1.

The stent was positioned at the target and then heated to 41° C. whereby the entire stent was transformed to austenite but for the previously-formed elbow regions, which remained martensitic. The stent remained in this state during its useful lifetime. To facilitate removal of the stent from use, it was heated to 45° C. to invoke the austenitic transformation in the previously-formed elbow regions. Accordingly, the hook was re-formed, grabbed by forceps and removed from the body.

EXAMPLE 4

Tooth Implant

Figure 3A:
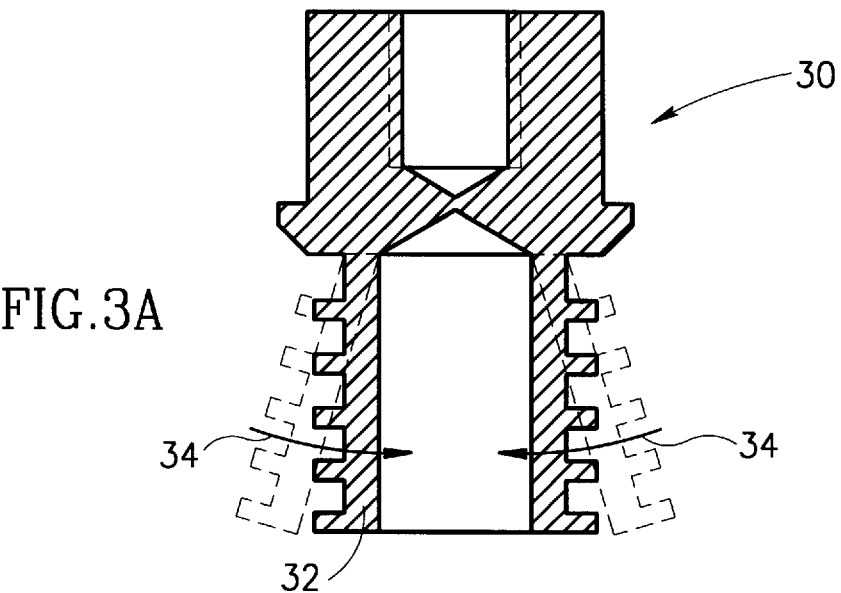
FIG. 3 shows a longitudinal cross-sectional view of a tooth implant at two states: austenitic state (FIG. 3A) and in a strain-induced martensite (FIG. 3B), deployed in a jaw bone.
Figure 3B:
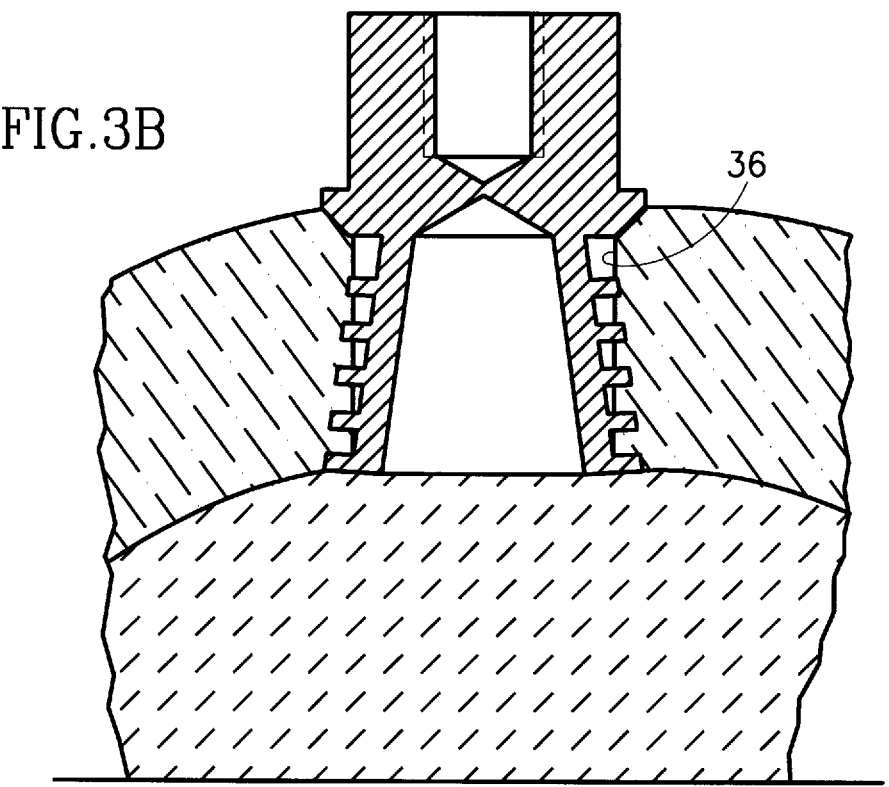

A tooth implant 30 shown in FIG. 3A consisting of an anchor portion 34 having leg-like protruding elements for fixation into the jaw bone was made from nitinol (50.5 at % Ni) after drawing at 500° C. and treating at 650° C. for 0.5 hour, 500° C. for 2 hours and 450° C. for 1.5 hours. The protruding elements 32 were straightened at 20° C. from an "open" configuration (represented by dashed lines in FIG. 3A) to a strained configuration (shaded in FIG. 3A), in the direction of arrows 34, to a strain of 5%, thus producing strain-induced martensite and resulting in an increase in the $A_s$ and $A_f$ temperatures to 39° C. and 42° C., respectively. The implant was then inserted into a root channel 36 (FIG. 3B) drilled in the jaw bone. The implant was exposed to 45° C. saline solution, thus inducing a transformation to austenite and changing the implant configuration to that shown in FIG. 3B to yield excellent anchoring into the jaw bone. Moreover, the implant applied a constant stress on the surrounding bone and was kept at a strain of up to 2%, at which $A_s=30°$ C. and $A_f=35°$ C.

EXAMPLE 5

Bone Fracture Healing Device

A compressive bone fracture healing device was made to include two screw-like segments with nitinol wire (50.8 at % Ni) in the interior of these segments. The wire was cold drawn to 0.5 mm in diameter, then annealed at 500° C. for 3 hours. The wire was stretched to a strain of 7%, resulting in the formation of strain-induced martensite and an increase in $A_s$ and $A_f$ to 39° C. and 41° C., respectively. The device was inserted into a fractured bone, where it was subjected to 1–2 ml of 45° C. saline solution to invoke a transformation to austenite. This transformation yielded a decrease in strain to approximately 3%, at which $A_s=30°$ C. and $A_f=34°$ C. Use of the device in this manner resulted in a constant compressive force on the fracture surface.

The above has been a detailed discussion of certain embodiments of the present invention. They should not be considered so as to limit the scope of applicants' invention which is defined by the appended claims.

We claim:

1. A medical device comprising a shape memory alloy (SMA) portion having an austenitic and a martensitic state with a different configuration in each of these states, the SMA being transformable from a martensitic to an austenitic state by an austenitic transformation occurring in a temperature range between $A_s$, a start temperature of the austenitic transformation, to $A_f$, a finish temperature of the austenitic transformation, and being transformable from an austenitic state to a martensitic state by a martensitic transformation occurring in a temperature range lower than body temperature between $M_s$, a start temperature of a martensitic transformation and $M_f$, a finish temperature of the martensitic transformation, $A_s$ being lower than body temperature in an undeformed state; the device being characterized in that:

the SMA portion is deformable from an undeformed first configuration assumed by it in the austenitic state to a deformed second configuration, such that the deformation converts it into a strain-induced martensitic or partial martensite with an increase in $A_s$ from its original temperature $A_s°$, to a temperature $A_s'$; and in that when the SMA portion, once in said second configuration, is heated to a temperature higher than $A_s'$, it transforms to an at least partial austenitic state, which transformation results in a change in configuration from the deformed second configuration towards the undeformed first configuration and in a decrease of $A_s$ from $A_s'$ to $A_s°$, such that the SMA portion is stable in the at least partial austenitic state at the body temperature.

2. A medical device according to claim 1, wherein the shape memory alloy is nitinol.

3. A medical device according to claim 1, wherein at least one portion of the SMA is deformable to a higher strain than the remainder of the SMA such that said at least one portion has an $A_s'$ temperature $t_2$ which is greater than the $A_s'$ temperature of the remainder SMA, $t_1$.

4. A medical device according to claim 3, to be deployed in the body by heating the SMA to a temperature higher than $t_1$ but less than $t_2$, whereby said at least one portion remains in a martensitic state during deployment and the remainder of the SMA transforms to austenitic.

5. A medical device according to claim 1, wherein $A_s'$ is above body temperature.

6. A medical device according to claim 1, wherein $A_s'$ is below body temperature and $A_f'$ is above body temperature.

7. A medical device according to claim 1, being a member of the group consisting of a medical stent, a tooth implant, a bone fracture healing device, a heart implant, a bone plate and an intrauterine contraceptive device.

8. A method of deploying a medical device within the human body, the medical device comprising a shape memory alloy (SMA) portion having an austenitic and a martensitic state with a different configuration in each of these states and having associated $M_s$, $M_f$, $A_s$ and $A_f$ temperatures, being start and finish temperatures of the SMA's martensitic transformation and the start and finish temperature of the SMA's austenitic transformation, respectively, $A_s$ having the value $A_s^\circ$ which being less than body temperature, when the medical device is in an undeformed state, and $M_s$ being less than $A_s$, the method comprising the steps of:

heating the SMA to a temperature greater than $A_s$, thereby placing the SMA in at least a partial austenitic state;

cooling the medical device to a temperature between $A_s$ and $M_s$;

deforming the medical device from an undeformed first configuration assumed by it in the austenitic state to a deformed second configuration, said deforming resulting in an increase in $A_s$ from $A_s^\circ$ to $A_s'$, the SMA portion being in a martensitic or partial martensitic state after said deforming;

positioning the medical device to a target location within the body, the SMA portion remaining in the martensitic or partial martensitic state during said positioning; and transforming the SMA portion from the martensitic or partial martensitic state to at least a partial austenitic state by heating it to a temperature higher than $A_s'$, said transforming resulting in a change in the configuration of the SMA portion from the deformed second configuration towards the undeformed first configuration, the change in configuration resulting in a decrease in $A_s$ from $A_s'$ to $A_s^\circ$ such that the medical device is stable in at least a partially austenitic state while deployed in the body.

9. A method according to claim 8, wherein the shape memory alloy is nitinol.

10. A method according to claim 8, wherein at least one portion of the SMA is deformed to a higher strain than the remainder of the SMA during said deforming, such that the at least one portion has an $A_s'$ temperature $t_2$, higher than the $A_s'$ temperature of the remainder of the SMA, $t_1$.

11. A method according to claim 10, wherein the SMA is heated to a temperature higher than $t_1$ but less than $t_2$ such that the at least one portion remain in a martensitic state and the remainder of the SMA transforms to austenite.

12. A method according to claim 11, further comprising heating the SMA to a temperature higher than $t_2$ after said transforming step, thereby transforming the at least one portion from a martensitic state to an austenitic state.

13. A method according to claim 11, further comprising removing the medical device from the body by gripping the at least one portion of a higher strain which had been transformed during heating to a temperature about $t_2$.

14. A method of deploying a medical device within the human body, the medical device comprising a shape memory alloy (SMA) portion having an austenitic and a martensitic state with a different configuration in each of these states and having associated $M_s$, $M_f$, $A_s$ and $A_f$ temperatures, being start and finish temperatures of the SMA's martensitic transformation and the start and finish temperature of the SMA's austenitic transformation, respectively, $A_s$ having the value $A_s^\circ$, which is less than body temperature, when the medical device is in an undeformed state, the method comprising the steps of:

deforming the medical device by transforming it from an undeformed first configuration assumed by it in the austenitic state to a deformed second configuration, said deforming resulting in an increase in $A_s$ from $A_s^\circ$ to $A_s'$, the SMA portion being in a strain-induced martensitic or partial martensitic state after said deforming;

positioning the medical device to a target location within the body, the SMA portion remaining in the strain-induced martensitic or partial martensitic state during said positioning; and transforming the SMA portion from said martensitic or partial martensitic state to at least a partial austenitic state by heating it to a temperature higher than $A_s'$, said transforming resulting in a change in the configuration of the SMA portion from the deformed second configuration towards the undeformed first configuration, the change in configuration resulting in a decrease in $A_s$ from $A_s'$ to $A_s^\circ$ such that the medical device is stable in at least a partially austenitic state while deployed in the body.

* * * * *